United States Patent
Foret et al.

(10) Patent No.: US 6,939,452 B2
(45) Date of Patent: Sep. 6, 2005

(54) PARALLEL SAMPLE LOADING AND INJECTION DEVICE FOR MULTICHANNEL MICROFLUIDIC DEVICES

(75) Inventors: Frantisek Foret, Malden, MA (US); Thomas Rejtar, Malden, MA (US); Bailin Zhang, Boston, MA (US); Barry L. Karger, Newton, MA (US)

(73) Assignee: Northeastern University, Boston, MA (US)

( * ) Notice: Subject to any disclaimer, the term of this patent is extended or adjusted under 35 U.S.C. 154(b) by 502 days.

(21) Appl. No.: 10/181,503
(22) PCT Filed: Jan. 18, 2001
(86) PCT No.: PCT/US01/01705
§ 371 (c)(1),
(2), (4) Date: Sep. 20, 2002
(87) PCT Pub. No.: WO01/53794
PCT Pub. Date: Jul. 26, 2001

(65) Prior Publication Data
US 2004/0031686 A1 Feb. 19, 2004

Related U.S. Application Data
(60) Provisional application No. 60/176,183, filed on Jan. 18, 2000.

(51) Int. Cl.[7] ............... G01N 27/447; G01N 27/453
(52) U.S. Cl. ............... 204/458; 204/451; 204/601; 204/644
(58) Field of Search ............... 204/601–605, 204/451–455, 644, 458; 422/99, 100, 103; 73/863.21, 863.32, 864.81

(56) References Cited

U.S. PATENT DOCUMENTS

| | | | |
|---|---|---|---|
| 5,872,010 A | 2/1999 | Karger et al. | 436/173 |
| 5,885,430 A | 3/1999 | Kernan et al. | 204/453 |
| 6,086,825 A | 7/2000 | Sundberg et al. | 422/100 |
| 6,110,332 A | 8/2000 | Swierkowski | 204/242 |
| 6,149,787 A | 11/2000 | Chow et al. | 204/426 |
| 6,165,417 A | 12/2000 | Swierkowski | 422/100 |
| 6,207,031 B1 | 3/2001 | Adourian et al. | 204/451 |

*Primary Examiner*—Alex Noguerola
(74) *Attorney, Agent, or Firm*—Weingarten, Schurgin, Gagnebin & Lebovici LLP

(57) ABSTRACT

A sample load and injection device (10) includes sample introduction capillaries (11) attached to a microfluidic device (12). Sample introduction capillaries (11) are connected to sample introduction channels (18). Sample introduction capillaries (18) are connected to separation channels (20) at connection points (21). At a defined distance along the separation channels (20), auxilliary channels (23) originate at connection points (24). The sample load and injection device includes cover plate (28) which has connecting channels (26, 32). Connecting channel (26) is associated with ends (24) of sample introduction channels (18). Connecting channel (32) is associated with ends (20).

11 Claims, 3 Drawing Sheets

Fig. 1 Scheme of parallel sample injection

PARALLEL SAMPLE LOADING AND INJECTION DEVICE FOR MULTICHANNEL MICROFLUIDIC DEVICES

CROSS REFERENCE TO RELATED APPLICATIONS

This application claims the priority of U.S. Provisional Application No. 60/176,183 filed Jan. 18, 2000, and of PCT International Patent Application No. PCT/US00/09480 filed Apr. 10, 2000, the whole of which are hereby incorporated by reference herein.

STATEMENT REGARDING FEDERALLY SPONSORED RESEARCH OR DEVELOPMENT

Part of the work leading to this invention was carried out with United States Government support provided under a grant from the National Institutes of Health, Grant No. NIH (GM15847). Therefore, the U.S. Government has certain rights in this invention.

BACKGROUND OF THE INVENTION

Recent developments in microfabrication techniques have permitted the integration of microminiature tools for biochemical analysis within a tiny microfluidic device. Microfluidic devices have been successfully demonstrated as useful for a wide variety of separation techniques as well as for sample pretreatment and/or manipulation methods. Complete chemical processing systems, e.g., reaction chambers, separation capillaries and their associated electrode reservoirs, as well as certain types of detectors, can be consolidated on a microfluidic device or microchip. Such "labs-on-a-chip," in principle, permit effective utilization and manipulation of minute quantities of material. Systems have been developed that permit the efficient transfer of nanoliter quantities or other small quantities of a fluid sample from the spatially concentrated environment of a microfluidic device to "off-chip" analytical or collection devices without an increase in sample volume. (See, U.S. Pat. No. 5,872,010, the whole of which is hereby incorporated by reference herein.) However, methods for moving small quantities of samples from a sample vial or holder onto a chip or directly to an analytical device without either evaporation or dilution are less well developed.

One important issue for the further development of microfluidic devices is that sample introduction into a device and subsequent injection of a sample aliquot into, e.g., a separation channel or reaction compartment on the device must be carried out in a reliable, accurate and convenient manner. Moreover, the method should not result in any sample "cross talk" and should be easy to automate. This is very difficult to accomplish when multiple channels on one microfluidic device are used.

BRIEF SUMMARY OF THE INVENTION

The invention is directed to a universal interface and sample load and injection device, and to method for its use, for the parallel introduction and simultaneous or subsequent injection of liquid samples into channels of a multichannel microfluidic device. The sample load and injection device can be integral with a multichannel microfluidic device or can be a separately attachable entity. The sample load and injection device of the invention comprises a sample introduction capillary (and, preferably, multiple sample introduction capillaries), each said introduction capillary having an inlet end and an outlet end, the inlet end of each said individual capillary being external to said sample load and injection device and capable of being placed in alignment with one of multiple samples in a sample holder, e.g., one well in a 96-well microtiter plate, and the outlet end of each said introduction capillary opening to an introduction channel in said sample load and injection device, each introduction channel an end within the device. The sample load device further comprises a sample channel originating at each said introduction channel, an auxiliary channel originating at each said sample channel and ending at an auxiliary channel end within said sample load and injection device, a connecting channel connecting said introduction channel ends and a connecting channel connecting said auxiliary channel ends. The connecting channel for said introduction channel ends and the connecting channel for said auxiliary channel ends each terminates at a surface of said sample load device, and each said connecting channel is configured for connection to a source of positive or negative pressure or to a source for applying an electric field across any channel segment. The sample channels and the auxiliary channels are preferably smaller in internal diameter than the introduction channels.

In other embodiments, the connecting channels reside in a cover plate that is separable from the sample load and injection device body and at least one of the sample channels is configured for separation of a loaded sample. Separation can be of any kind, e.g., chromatographic (LC, CEC) or electrophoretic (CZE, IEF, MEKCC). Channels configured for separation can be equipped, e.g., for absorbance (UV, Vis), fluorescence, conductivity, electrochemical detection or for sample collection or transfer to external devices such as MALDI/TOF. Furthermore, the sample load and injection device can include an electrospray interface chamber coupled to the outlet end of one of the sample introduction channels.

The sample load and injection device of the invention is suitable for moving small quantities of samples from, e.g., the wells of a 96-well microtiter plate (or any other sample plate size), onto a microfluidic device or directly to an analytical device, without either evaporation or dilution, and for, e.g., sample preconcentration, entrapment or preseparation prior to further manipulation on the microdevice. The sample introduction (or loading) capillaries can be packed with any suitable material (e.g., chromatographic beads or polymeric monolith, affinity material, immobilized enzyme material, etc.) or coated with any kind of coating so that, e.g., most of the components of the sample (or only selected components) can be trapped or digested inside the loading capillaries. After trapping, the sample constituents can be eluted into the channels inside the microdevice with the use of a suitable eluent. Selective stepwise or gradient elution can be applied to elute only certain sample components at a time. Individual sample loading capillaries can contain different packing materials and have different internal volumes so that different sample volumes can be handled in individual channels of the accompanying microfluidic device. Additionally, the sizes of the channels inside the microfluidic device can be optimized so that different flow rates are generated upon application of a pressure or electric field. This flexibility is useful to increase the dynamic range of an analysis carried out using the device of the invention. If the packing inside individual sample loading capillaries is not functionalized, it can, at least, serve as a particle filter to prevent clogging of channels internal to the device. The sample loading capillaries can be designed either as integral parts of the device (e.g., pulled from the device) or as separately attachable entities. They can be reusable or disposable.

A sample loading and injection device can be made of any etchable or moldable material. Preferably, the material is a transparent plastic or glass (e.g., silicon). Various metals are useful for certain applications.

The samples may be transfered using the sample loading and injection device of the invention for electrospray-mass spectrometry analysis (ESI/MS), for atmospheric pressure-chemical ionization mass spectrometry analysis (APCI/MS), for matrix assisted laser desorption ionization mass spectrometry (MALDI/MS), for nuclear magnetic resonance analysis (NMR), for pneumatically or ultrasonically assisted spray sample handling, for transfer to an off-chip detection system, such as electrochemistry, conductivity or laser induced fluorescence, or for collection of specific fractions, e.g., in collection capillaries or on collection membranes.

The channels of any microfluidic device used with the sample load mechanism of the invention may be arrayed in any format that allows for sequential or simultaneous processing of liquid samples, as desired.

In any embodiment, each channel may include electrical contacts, so that an electric circuit path can be established along the channel. For example, one electrical contact can be on the entrance side of a channel and another electrical contact can be on the exit side. In an alternative arrangement, an electric circuit can be completed by an external contact, beyond the exit end of the channel. For example, if the exit port of a channel is used as an electrospray source for a mass spectrometer, the mass spectrometer sampling orifice can serve as the counter electrode. Samples can be transferred off chip for subsequent analysis by switching the electric current sequentially to each channel on the chip.

Samples can be introduced into a channel on a microfluidic device by the sample loading and injection device of the invention by a variety of methods, e.g., by pressure, electrokinetic injection, or other technique, and an electrical current and/or pressure drop can then be applied to cause the sample components to migrate along the channel. The channels may function only for fluid transfer, e.g., to a mass spectrometer, or the channels can serve as environments for various types of sample manipulations, e.g., for micropreparative or analytical operations, such as capillary electrophoresis (CE), chromatography or the polymerase chain reaction (PCR), or for carrying out any type of sample chemistry. The channels may be filled with membrane or packing material to effectuate preconcentration or enrichment of samples or for other treatment steps, such as desalting. Furthermore, other modification of sample components, e.g., by enzymes that are covalently bound to the walls of a channel or are free in a channel, are possible. Packing material may be bound to the walls of the channels or may include other components, such as magnetic particles, so that when a magnetic field is applied, the magnetic particles retain the packing material in place. The magnetic particles can also be used for efficient mixing of fluids inside the channels, using an external magnetic field. A micromachined filter or other stationary structure may also be employed to hold packing material in place. Alternatively, stationary structures can be micromachined, cast or otherwise formed in the surface of a channel to provide a high surface area which can substitute for packing material.

A sample can be introduced into a channel in a short starting zone or can fill the whole channel completely. Filling only a small part of the channel with the sample is preferable when an on-chip separation of sample components is to be carried out, such as electrophoresis or chromatography. Filling the whole channel with the sample may be advantageous in cases when off-chip analysis requires extended sample outflow, such as sample introduction/electrospray ionization for structure analysis by mass spectrometry.

In many cases a liquid flow may be required to transport the analytes in a sample into a specific channel, or along the length of the channel, or out of the channel via an exit port. Therefore, to assist in the required fluid transfer, a pumping device may be incorporated into or associated with the microscale device of the invention. For example, a heating element can be used to cause thermal expansion, which will effectuate sample liquid movement, or a heating element can be used to generate a micro bubble, the expansion of which causes the sample to travel in the channel. Other options may include pumping by the pressure of a gas or gases generated by on-chip electrolysis. Flow can be also generated by application of a pressure drop along a channel or by electroosmosis inside a channel.

As samples move to the end of a channel, they can be subjected to detection or analysis at a site external to the microscale device of the invention by a variety of techniques, including mass spectroscopy, nuclear magnetic resonance, laser induced fluorescence, ultraviolet detection, electrochemical detection, or the like. The end of each channel may include a tip configured to facilitate transfer of the sample volume.

Different sized channels may be employed on the same accompanying microfluidic device. For example, larger channels may be used for cleanup operations, and smaller channels may be used for processing operations. Moreover, other operations can be performed in other regions of the device, such as chemical processing, separation, isolation or detection of a sample or a component of the sample, prior to sample loading in a channel. Thus, it is possible to carry out sample chemistries or to conduct micropreparative and analytical operations on both a starting sample and its separated components within the device of the invention, prior to transfer of the sample or its components off chip for further analysis or collection. Additionally, detection of a sample may be carried out on the microfluidic device itself, e.g., by a fiber optic detection system, which can provide complementary control information for off-chip analysis and detection, or by any other suitable detector such as laser induced fluorescence, conductivity and/or electrochemical detector.

Other features and advantages of the invention will be apparent from the following description of the preferred embodiments thereof and from the claims.

BRIEF DESCRIPTION OF THE SEVERAL VIEWS OF THE DRAWING

FIG. 1a is a plan view of a sample load and injection device according to the invention;

FIG. 1b is a section through the sample load and injection device of FIG. 1a;

DESCRIPTION OF THE PREFERRED EMBODIMENT OF THE INVENTION

The parallel sample load and injection device of the invention allows for a simple automated way of transferring samples from a standard, e.g., 96-well, microtiter plate into a microfluidic device and for the simultaneous or subsequent injection of samples into multiple channels on the device.

Figure 1:
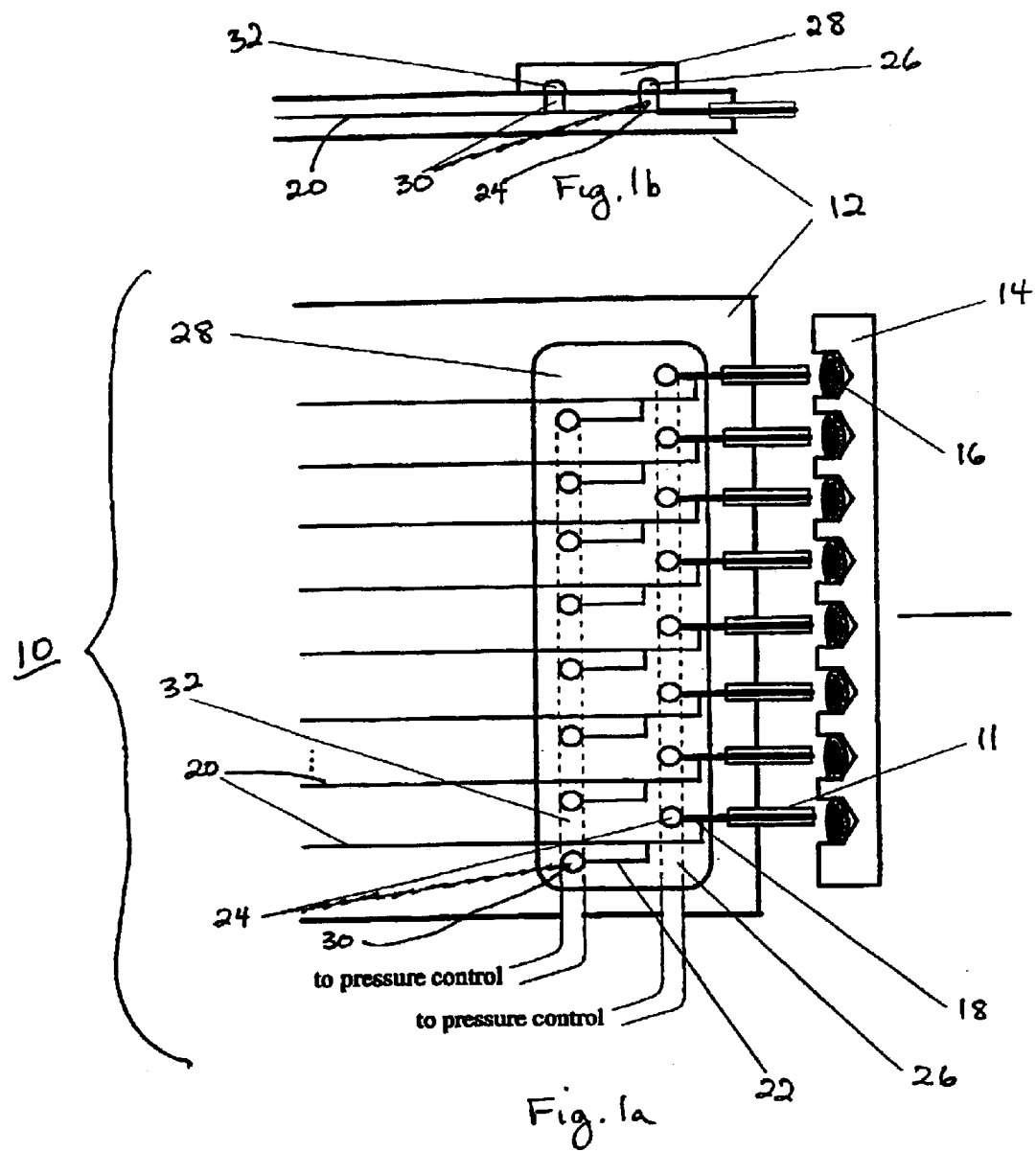
Figure 2:
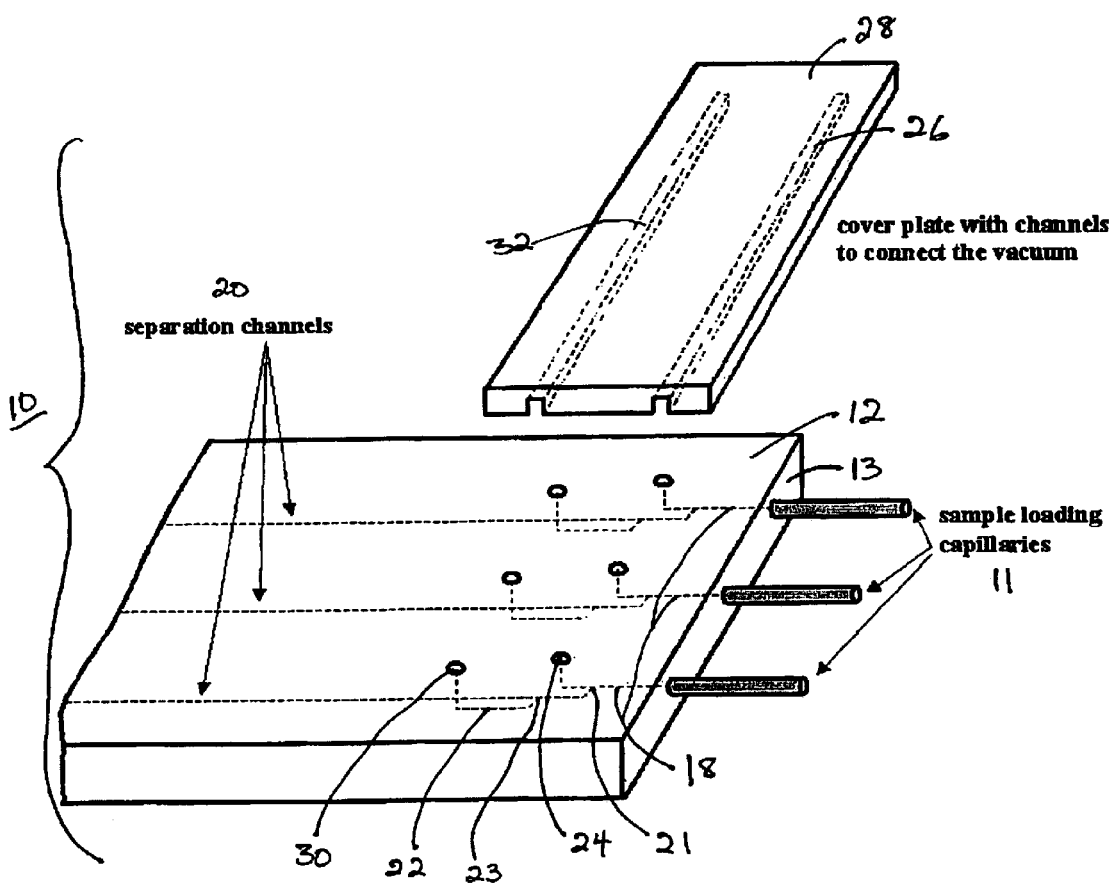
FIG. 2 is an exploded perspective view of a sample load and injection device according to the invention.
Figure 3:
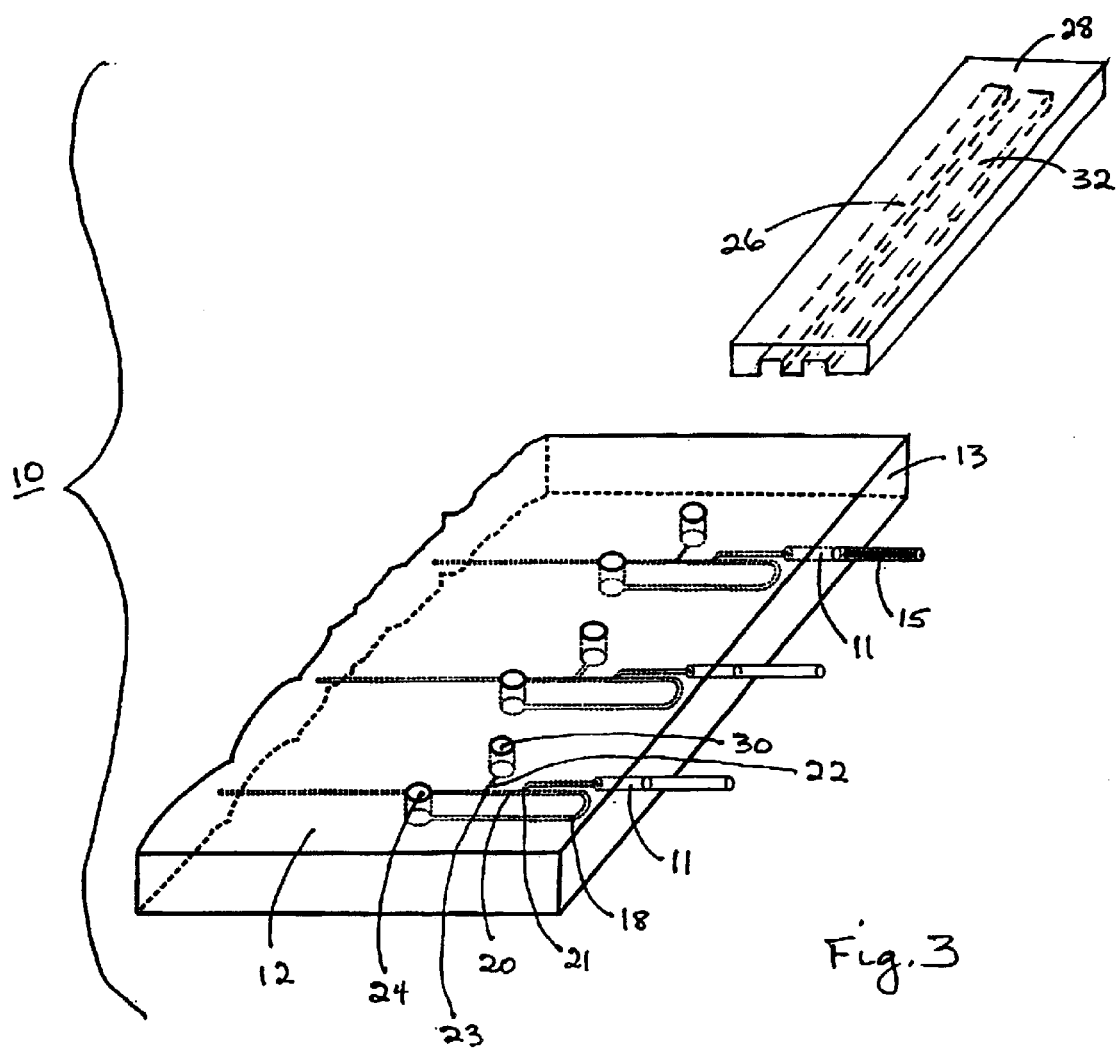
FIG. 3 is an exploded perspective view of another embodiment of a sample load and injection device according to the invention.

Referring to FIGS. 1a–3, a sample load and injection device (10) includes parallel sample introduction capillaries (11) that are attached to a microfluidic device (12) into which the sample load and injection device of the invention is integrated. The spacing between these capillaries is compatible with the spacing of the wells in standard microtiter plates (14). As indicated in FIG. 3, individual sample introduction capillaries (11) may contain packing material (15) for sample pretreatment.

Sample solutions in individual wells (16) are transferred through introduction capillaries (11) into introduction channels (18) in the sample load and injection device. Each of the sample introduction channels (18) is connected to the appropriate sample separation channel (20), at connection point (21). At a defined distance along the separation channel, an auxiliary channel (22), which aids in sample injection as will be described below, originates at connection point (23). The distance between these two connection points determines the length of the sample injection "plug." All sample introduction channels are connected through introduction channel ends (24) to a connecting channel (26) made in associated cover plate (28), which is attachable to device (12). Channel (26) is used for applying negative pressure (a vacuum) simultaneously to all sample introduction channels (18). A similar connection is made among associated auxiliary channel ends (30), using connecting channel (32). Sample separation channels (20) and auxiliary channels (22), (generally 200–1000 $\mu$L in internal diameter and preferably approximately 500 $\mu$L) are preferably smaller in internal diameter than introduction channels (18), which are generally 20–100 $\mu$L (and preferably 50 $\mu$L) in internal diameter.

In one embodiment, sample loading and injection can be carried out in the following manner: the channels of the microfluidic device are first flushed with background electrolyte, and then the device is positioned in front of a microtiter plate so that the sample introduction capillaries (11) are immersed into individual sample wells. A vacuum is applied to connection channel (26), which connects introduction channel ends (24). The different samples simultaneously fill the sample introduction channels (18), but due to hydrodynamic resistance, do not enter the smaller sample separation channels (20). This is the loading step. Subsequently, in a similar manner, connection channel (32) is used for application of a vacuum to all auxiliary channels so that the samples are pulled through a portion of the separation channels into the auxiliary channels; this is the injection step. After this step, the microtiter plate is replaced by a reservoir containing background electrolyte. A vacuum is then again applied to the sample introduction channels (18), via connecting channel (26), so that the content of these channels is exchanged for background electrolyte. The sample injection "plugs," i.e., those portions of the samples that were introduced into the sections of the separation channels between connection points (21) and (23), remain unchanged since the high hydrodynamic resistance of the channels (20) and (22) minimizes sample flow. (Sample also remains in auxiliary channels (22).) Subsequently, e.g., in order to separate the components of the sample in the sample plugs, an electrical potential is applied across the separation channels.

The method of the invention can also be carried out in a manner that combines the loading and injection steps. In this procedure, a vacuum is applied first to connection channel (32) so that the individual samples are pulled directly through a portion of loading channels (18) and separation channels (20) and into auxiliary channels (22). For practice of this method of the invention, the separation and auxiliary channels need not be smaller in internal diameter than the loading channels. Simultaneous loading and injection of samples is a faster procedure. Sequential loading and injection steps are useful when it is desirable to carry out, e.g., sample preconcentration, entrapment or preseparation in the loading capillaries prior to sample injection.

The disclosed sample introduction and injection procedure will be useful for any device designed for handling and analysis of small amounts of samples, especially in genomics and proteomics. The parallel sample load and injection device and method of the invention allow for a simple automated way for the transfer of samples from a standard microtiter plate into a microfluidic device and simultaneous injection into multiple channels on the device. The method of the invention has been described for hydrodynamic sample injection followed by electrophoretic separation. However, the method of the invention can be also used for electrokinetic injection and for any other kind of separation or manipulation technique.

The sample load mechanism of the invention permits more efficient use of powerful analytical devices, such as the mass spectrometer, than is currently possible. In addition, the system of the invention can be manufactured as a disposable device that is suitable for cost effective automation of the analysis of a large number of samples. Using this micromachined approach, high throughput analysis by mass spectrometry would be possible. In addition, handling of small volumes and quantities of samples would be facilitated, and consumption of valuable samples and reagents would be reduced. Applications include any laboratory analysis methods, especially where high throughput and minimization of cross-contamination are desirable, such as screening and diagnostic methods, and such other analytic methods as pharmacokinetics where fresh columns are required for each run.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A sample load and injection device for the parallel transfer of liquid samples into channels of a multichannel microfluidic device, said sample load and injection device comprising:

multiple sample introduction capillaries, each said introduction capillary having an inlet end and an outlet end, the inlet end of each said individual capillary being external to said sample load and injection device and capable of being placed in alignment with one of multiple samples in a sample holder, and the outlet end of each said introduction capillary opening to an introduction channel in said sample load and injection device, said introduction channel having an introduction channel end in said sample load and injection device;

a sample channel originating at each said introduction channel;

an auxiliary channel originating at each said sample channel and ending at an auxiliary channel end in said sample load and injection device;

a connecting channel connecting said introduction channel ends; and a connecting channel connecting said auxiliary channel ends, said connecting channel for said introduction channel ends and said connecting channel for said auxiliary channel ends each terminating at one end at a surface of said sample load and injection device, wherein each said connecting channel is configured for connection to a source of positive or negative pressure or to a source for applying an electric field across any channel segment.

2. The sample load and injection device of claim 1, wherein said sample channels and said auxiliary channels are smaller in internal diameter than are said introduction channels.

3. The sample load and injection device of claim 1, wherein said connecting channels are resident in a cover plate that is separable from the main body of said sample load and injection device.

4. The sample load and injection device of claim 1, wherein said one or more of said sample channels is configured for separation of a loaded sample.

5. The sample load and injection device of claim 1, wherein said sample load and injection device is integral with a multichannel microfluidic device.

6. The sample load and injection device of claim 1, wherein said sample load and injection device is separable from but attachable to a multichannel microfluidic device.

7. A method for the parallel injection of samples into separate channel systems within a microfluidic device, said method comprising the steps of:

providing the sample load and injection device of claim 1;

positioning said sample load and injection device adjacent a sample holder having multiple individual samples so that individual sample introduction capillaries of said device are immersed into individual samples in said sample holder;

applying a vacuum to said connecting channel connecting said auxiliary channel ends, wherein said individual samples are pulled through said introduction channels and a portion of each of said separation channels and into said auxiliary channels; and replacing said individual samples in said sample holder by a reservoir containing a background electrolyte and applying a vacuum to said connecting channel connecting said introduction channel ends, whereby the portions of said samples remaining in said introduction capillaries and said introduction channels are replaced by said background electrolyte.

8. The method of claim 7, wherein, prior to the step of applying a vacuum to said connecting channel connecting said auxiliary channel ends, said method further comprises the step of applying a vacuum to said connecting channel connecting said introduction channel ends, wherein said individual samples simultaneously fill said individual sample introduction capillaries and associated sample introduction channels.

9. The method of claim 7 or claim 8, wherein, prior to said positioning step, said method further comprises the step of flushing said channels of said device with background electrolyte.

10. The method of claim 7 or claim 8, wherein said sample introduction capillaries comprise a coating or a packing material and said samples are exposed to said coating or to said packing material during passage through said introduction capillaries.

11. The method of claim 7 or claim 8, wherein samples in said introduction capillaries are subjected to an isoelectrofocusing step.

* * * * *